US011298076B2

(12) United States Patent
Ochs et al.

(10) Patent No.: US 11,298,076 B2
(45) Date of Patent: Apr. 12, 2022

(54) METHODS AND SYSTEMS FOR ALERTING PRACTITIONERS TO PHYSIOLOGICAL CONDITIONS

(71) Applicant: COVIDIEN LP, Mansfield, MA (US)

(72) Inventors: James Ochs, Seattle, WA (US); Scott Amundson, Oakland, CA (US); Keith Batchelder, New York, NY (US)

(73) Assignee: COVIDIEN LP, Mansfield, MA (US)

( * ) Notice: Subject to any disclaimer, the term of this patent is extended or adjusted under 35 U.S.C. 154(b) by 491 days.

(21) Appl. No.: 16/119,770

(22) Filed: Aug. 31, 2018

(65) Prior Publication Data

US 2018/0368759 A1 Dec. 27, 2018

Related U.S. Application Data

(60) Continuation of application No. 14/825,982, filed on Aug. 13, 2015, now Pat. No. 10,076,276, which is a
(Continued)

(51) Int. Cl.
*A61B 5/00* (2006.01)
*A61M 16/06* (2006.01)
(Continued)

(52) U.S. Cl.
CPC .......... *A61B 5/4818* (2013.01); *A61B 5/002* (2013.01); *A61B 5/0205* (2013.01);
(Continued)

(58) Field of Classification Search
CPC ..... A61B 5/4818; A61B 5/002; A61B 5/0205; A61B 5/14551; A61B 5/7246;
(Continued)

(56) References Cited

U.S. PATENT DOCUMENTS 3,638,640 A 2/1972 Shaw
3,926,177 A 12/1975 Hardway, Jr. et al.
(Continued)

FOREIGN PATENT DOCUMENTS

DE 19640807 9/1997
EP 178197 5/1989
(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).
(Continued)

*Primary Examiner* — Devin B Henson
(74) *Attorney, Agent, or Firm* — Cantor Colburn LLP

(57) ABSTRACT

Embodiments of the present disclosure provide systems and methods for monitoring a patient to produce a signal representing a blood oxygen concentration. The signal may be analyzed to determine the presence of one or more sleep apnea events, and an integral of the signal may be calculated if the signal is outside of a set range or threshold. A practitioner may choose to be informed of the presence of sleep apnea events if the blood oxygen concentration is less then a preset limit, if an upper limit has been reached for an integral representing the severity of the oxygen deprivation over time, or anytime sleep apnea events may be present in the signal.

19 Claims, 9 Drawing Sheets

Related U.S. Application Data continuation of application No. 14/286,269, filed on May 23, 2014, now Pat. No. 9,107,635, which is a division of application No. 12/388,123, filed on Feb. 18, 2009, now Pat. No. 8,750,953.

(60) Provisional application No. 61/066,182, filed on Feb. 19, 2008.

(51) Int. Cl.
*A61M 16/00* (2006.01)
*A61B 5/024* (2006.01)
*A61B 5/1455* (2006.01)
*G08B 21/04* (2006.01)
*A61B 5/0205* (2006.01)
*A61B 5/145* (2006.01)

(52) U.S. Cl.
CPC ...... *A61B 5/14551* (2013.01); *A61B 5/14552* (2013.01); *A61B 5/7246* (2013.01); *A61B 5/7278* (2013.01); *A61B 5/7282* (2013.01); *A61B 5/742* (2013.01); *A61B 5/7405* (2013.01); *A61B 5/746* (2013.01); *A61B 5/7475* (2013.01); *A61M 16/0051* (2013.01); *A61M 16/021* (2017.08); *A61M 16/06* (2013.01); *G08B 21/0453* (2013.01); *A61B 5/02416* (2013.01); *A61B 5/1455* (2013.01); *A61B 5/14542* (2013.01); *A61M 2205/18* (2013.01); *A61M 2205/50* (2013.01)

(58) Field of Classification Search
CPC . A61B 5/7278; A61B 5/7282; A61B 5/02416; A61M 16/021; A61M 16/0051
See application file for complete search history.

(56) References Cited

U.S. PATENT DOCUMENTS

| | | |
|---|---|---|
| 4,696,307 A | 9/1987 | Montgieux |
| 4,714,341 A | 12/1987 | Hamaguri et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |
| 5,143,078 A | 9/1992 | Mather et al. |
| 5,167,230 A | 12/1992 | Chance |
| 5,190,038 A | 3/1993 | Polson et al. |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,398,682 A | 3/1995 | Lynn |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,605,151 A | 2/1997 | Lynn |
| 5,611,337 A | 3/1997 | Bukta |
| 5,630,413 A | 5/1997 | Thomas et al. |
| 5,632,272 A | 5/1997 | Diab et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Keunstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,865,736 A | 2/1999 | Baker et al. |
| 5,871,442 A | 2/1999 | Madarasz et al. |
| 5,873,821 A | 2/1999 | Chance et al. |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,064,898 A | 5/2000 | Aldrich |
| 6,070,098 A | 5/2000 | Moore-Ede et al. |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,223,064 B1 | 4/2001 | Lynn et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,584,336 B1 | 6/2003 | Ali et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |

(56) References Cited

U.S. PATENT DOCUMENTS

| | | | |
|---|---|---|---|
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,748,252 B2 | 6/2004 | Lynn et al. | |
| 6,754,516 B2* | 6/2004 | Mannheimer | A61B 5/02455 600/309 |
| 6,760,608 B2 | 7/2004 | Lynn | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,918,878 B2 | 7/2005 | Brodnick | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,127,278 B2 | 10/2006 | Melker et al. | |
| 7,162,306 B2 | 1/2007 | Caby et al. | |
| 7,190,261 B2 | 3/2007 | Al-Ali | |
| 7,190,995 B2 | 3/2007 | Chervin et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,373,193 B2 | 5/2008 | Al-Ali et al. | |
| 7,507,207 B2 | 3/2009 | Sakai et al. | |
| 7,639,145 B2 | 12/2009 | Lawson et al. | |
| 8,187,201 B2 | 5/2012 | Lynn | |
| 8,750,953 B2 | 6/2014 | Ochs et al. | |
| 8,932,227 B2 | 1/2015 | Lynn | |
| 9,107,635 B2 | 8/2015 | Ochs et al. | |
| 10,076,276 B2 | 9/2018 | Ochs et al. | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2004/0254481 A1 | 12/2004 | Brodnick | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0155206 A1 | 7/2006 | Lynn | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2007/0179369 A1 | 8/2007 | Baker, Jr. | |
| 2007/0191697 A1* | 8/2007 | Lynn | A61B 5/4818 600/323 |
| 2007/0282212 A1 | 12/2007 | Sierra et al. | |
| 2008/0097175 A1 | 4/2008 | Boyce et al. | |

FOREIGN PATENT DOCUMENTS

| | | |
|---|---|---|
| EP | 0615723 | 9/1994 |
| EP | 0630203 | 12/1994 |
| EP | 1491135 | 12/2004 |
| EP | 1740095 | 1/2007 |
| EP | 1821076 | 8/2007 |
| JP | 63275325 | 11/1988 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 10216115 | 8/1998 |
| JP | 2004194908 | 7/2000 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 A | 7/2004 |
| JP | 2004202190 | 7/2004 |
| JP | 2004248819 | 9/2004 |
| JP | 2004290545 | 10/2004 |
| JP | 2005034472 | 2/2005 |
| WO | WO9101678 | 2/1991 |
| WO | WO9221281 | 12/1992 |
| WO | WO9309711 | 5/1993 |
| WO | WO9403102 | 2/1994 |
| WO | WO9512349 | 5/1995 |
| WO | WO9639927 | 12/1996 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO0176471 | 10/2001 |

(56) References Cited

FOREIGN PATENT DOCUMENTS

| WO | WO03039326 | 5/2003 |
|---|---|---|
| WO | WO2005009221 | 2/2005 |
| WO | WO05096931 | 10/2005 |
| WO | WO08122806 | 10/2008 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19$^{th}$ International Conference IEEE-EMBS*, Oct. 30-Nov. 2, 1997; pp. 2326-2329.

Pickett, John, et al.; "Pulse Oximetry and PPG Measurements in Plastic Surgery," *Proceedings—19$^{th}$ International Conference—IEEE-EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engie in Medicine and Biology Society*, vol. 20, No. 6, p. 3072-3075, 1998.

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES-EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Yao, Jianchu, et al.; "Design of a Plug-and-Play Pulse Oximeter," *Proceedings of the Second Joint EMBS-BMES Conference*, Houston, Texas, Oct. 23-26, 2002; pp. 1752-1753.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

(56) References Cited

OTHER PUBLICATIONS

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Relente, A.R., et al.; "Characterization and Adaptive Filtering of Motion Artifacts in Pulse Oximetry using Accelerometers," *Proceedings of the Second joint EMBS-BMES Conference*, Houston, Texas, Oct. 23-26, 2002; pp. 1769-1770.

R. Neumann, et al.; "Fourier Artifact suppression Technology Provides Reliable $SpO_2$," *Abstracts*, A11, p. S105 (undated).

"Dimension XPS Details" Dell Computers Apr. 30, 2004. accessed Jun. 6, 2013 via internet archive wayback machine at http://web.archive.org/web/2040430030153/http://www1.us.dell.com/content/products/productdetails.aspx/d>, pp. 1-2.

\* cited by examiner

METHODS AND SYSTEMS FOR ALERTING PRACTITIONERS TO PHYSIOLOGICAL CONDITIONS

CROSS-REFERENCE TO RELATED APPLICATIONS

This application is a continuation of U.S. application Ser. No. 14/825,982, filed Aug. 13, 2015, which is a continuation of U.S. application Ser. No. 14/286,269, filed May 23, 2014, now U.S. Pat. No. 9,107,635, which is a divisional of U.S. application Ser. No. 12/388,123, filed Feb. 18, 2009, now U.S. Pat. No. 8,750,953, which claims priority to U.S. Provisional Application No. 61/066,182, filed Feb. 19, 2008, the disclosures of which are hereby incorporated in their entirety for all purposes.

BACKGROUND

The present disclosure relates to a system and method for alerting users to physiological conditions, more particularly, to a medical device configured to inform a user of the presence of patterns that may indicate the presence of sleep apnea.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Obstructive sleep apnea is a condition in which a patient's breathing is temporarily interrupted when sleeping. The condition is believed to be associated with increased fat deposits in the neck, which commonly occur as a patient ages. These increased fat deposits may lead to a narrowing of the airway. When muscle tone diminishes during sleep, the narrowed airway can collapse during inhalation, effectively blocking air movement. The patient attempts to inhale more deeply, further collapsing the airway. With no air movement, the oxygen level in the patient's bloodstream falls, finally reaching a point where the patient is aroused out of sleep. Upon arousal, the muscle tone increases, the airway opens, and air flow to the lungs is precipitously restored. The patient hyperventilates, which quickly restores the blood oxygen levels to normal levels. The period of arousal may be brief, so the patient is often unaware that the event took place. The patient returns to sleeping, and the cycle often repeats.

Over the years, this repeating cycle of low oxygen levels in the bloodstream can damage the heart and lead to other medical complications. Obstructive sleep apnea is believed to be one of the most common disorders in the United States. However, unlike other common medical disorders, such as diabetes, no simple diagnostic test has been developed to determine if a patient has sleep apnea. Tests do exist that can be used to diagnose sleep apnea, but the tests typically involve an overnight sleep study, which can be costly and inconvenient. The need for a simple, low-cost diagnostic test has led medical personnel to try less expensive techniques, such as pulse oximetry, to diagnose the presence of obstructive sleep apnea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical devices may be used to obtain or calculate signals representing physiological parameters from patients, such as $SpO_2$ signals related to a patient's level of blood oxygenation. However, these signals, which are sequences of numerical values of a physiological parameter over time, may have too much information or noise to be effectively used in the diagnosis or treatment of certain medical conditions. Accordingly, the signals may be processed to generate alerts, which may provide a more useful representation of the status of the medical condition. Embodiments of the present techniques provide methods that may be useful for generating indicators of a physiological status, based on a signal representing the blood oxygen saturation ($SpO_2$) level in a patient and, thus, alerting a practitioner to physiologically important conditions.

The indicators may be directly related to the presence of obstructive sleep apnea and may assist practitioners in the diagnosis and treatment of this condition. In embodiments, $SpO_2$ data collected on a pulse oximeter may be used to calculate or determine the alerts. The relative simplicity of this device could enhance the diagnosis of obstructive sleep apnea by allowing patients to take diagnostic equipment home for use overnight and return the equipment to a practitioner for analysis and diagnosis.

Previous studies have examined the possibility of generating a single index reflective of sleep apnea from pulse oximetry data, such as an airway instability index, but many have used schemes that may either be challenging for a practitioner to implement in a treatment setting or overly sensitive to changes. As embodiments may be implemented using current medical devices, their implementation may be easier to explain and use than a more complex calculation for an airway instability index.

Figure 1:
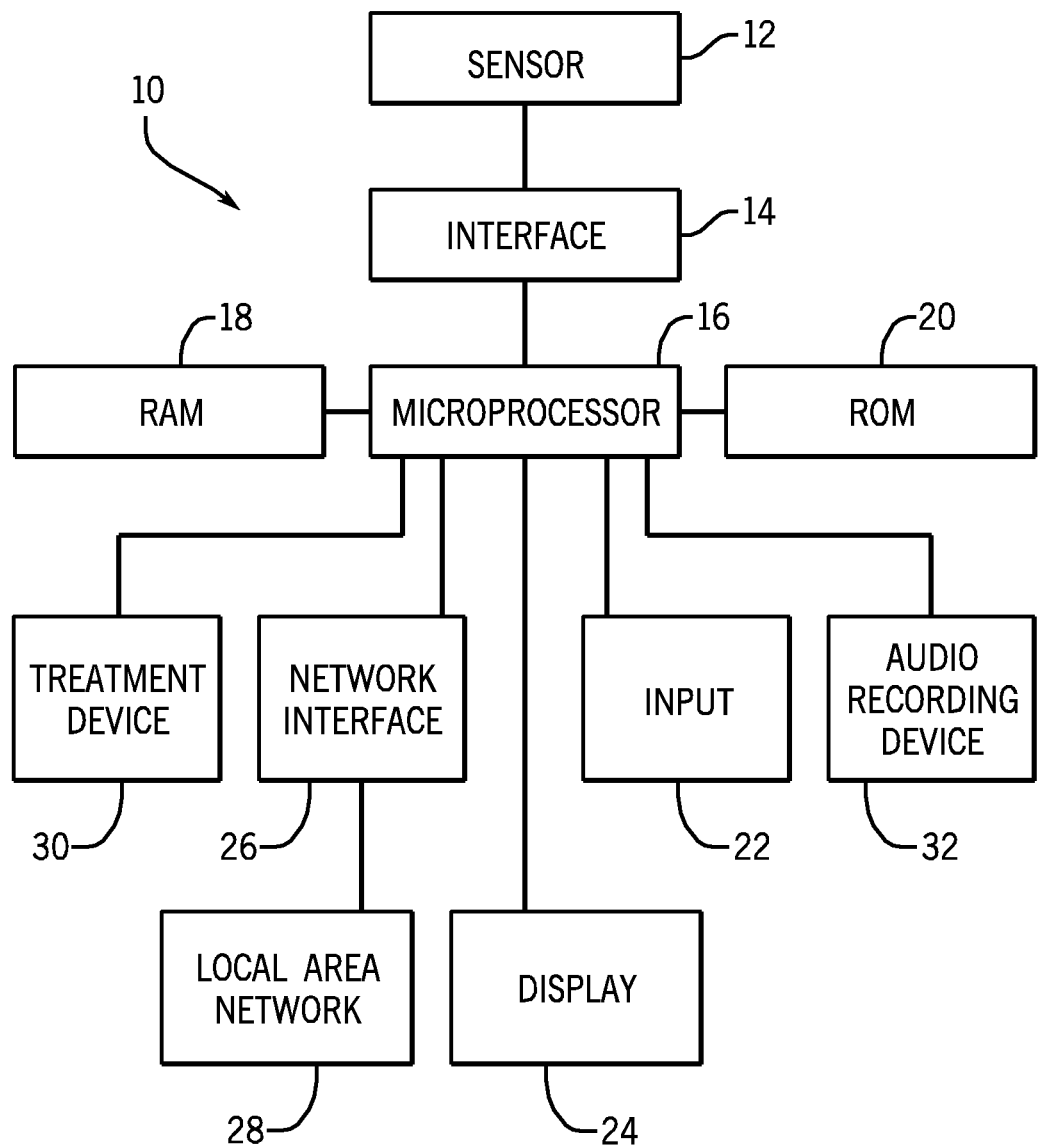
FIG. 1 is a block diagram of a system that may be used for the diagnosis and treatment of sleep apnea, in accordance with an embodiment.

FIG. 1 is a block diagram of a medical device 10, which may be used in embodiments of the present disclosure. The medical device 10 may have a sensor 12 for the collection of a signal representing a physiological parameter. In embodiments, the sensor 12 may be an optical sensor used with a pulse oximeter for the measurement of oxygen saturation in the bloodstream. The signal from the sensor 12 may be conditioned by an interface 14 prior to being utilized by a microprocessor 16. The microprocessor 16 may be coupled to random access memory (RAM) 18 and/or read-only memory (ROM) 20. The RAM 18 may be used to store the signals from the sensor 12 and the results of calculations that the microprocessor 16 performs. The ROM 20 may contain code to direct the microprocessor 16 in collecting and processing the signal. The microprocessor 16 may be coupled to an input device 22 which may be used for local entry of control and calculation parameters for the medical device 10. A display unit 24 may be coupled to the microprocessor 16 to display the results the microprocessor 16 has generated from the signal.

The microprocessor 16 may also be coupled to a network interface 26 for the transfer of data from the microprocessor 16 to devices coupled to a local area network 28. The transferred data may, for example, include signal data, indices including an airway instability index, alert signals, alarm signals, or any combination thereof. The transferred data may also consist of control signals from the devices on the local area network 28, for example, to instruct the medical device 10 to send signal data, or other information, to a device on the local area network 28.

In an embodiment, the medical device 10 may be used to alert a practitioner to a physiological condition using data collected from the sensor 12. The alert may be output to the display unit 24 or sent to a network device on the local area network 28. The processing may take place in real time, or may be run after the data collection may be completed for later identification of the physiological condition.

In another embodiment, a network device located on the local area network 28 may be configured to alert a practitioner to the presence of a physiological condition using the data collected from the sensor 12. In this embodiment, the network device may request that the signal be sent from the medical device 10 through the network interface 26. As for the embodiment discussed above, the network device may be used to either determine the alert signal in real time or to process a previously collected signal for later identification of the physiological condition.

In either of the embodiments above, the alert signals may appear on devices on the local area network 28, for example, a patient monitoring screen in an ICU. Alternatively, the alert signals may appear on the display unit 24 of the medical device 10. In embodiments, an alert signal may be activated in both locations using the results from either a local calculation on the medical device 10 or from a remote calculation on a network device coupled to the local area network 28.

The microprocessor 16 may also be coupled to a treatment device 30. For example, the treatment device 30 may be a positive pressure mask used to supply air at an increased pressure to maintain an open airway. In an embodiment, the treatment device 30 may be controlled by the microprocessor 16, for example, activating the treatment device 30 to open an airway based on the alert signals. This control may be useful in helping to confirm a diagnosis of obstructive sleep apnea, as restoration of the airway may restore blood oxygen levels to more normal levels.

A diagnosis of sleep apnea may also be aided by the sound the patient may be making during the sleep apnea events. For example, cessation of breathing following by a sudden gasping intake of breath may provide or confirm the diagnosis. However, such events may be irregularly spaced or may be separated by large time intervals, making any continuous audio recording of the patient tedious and/or expensive to analyze. An audio recording device 32 may be coupled to the microprocessor 16 for recording sounds made by the patient. In an embodiment, the microprocessor 16 may activate the audio recording device 32 based on the alert signals and record patient sounds when a sleep apnea event may be likely to be occurring. When combined with the alert signals, the sound recordings are likely to provide a positive diagnosis of obstructive sleep apnea.

Exemplary embodiments activate alert signals on the value of two general conditions. The first condition may be the presence or absence of clusters in the $SpO_2$ signal, as discussed below. The second condition may be the value of an integral calculated from the absolute level of the $SpO_2$ signal in comparison to previous set limits. The determination of these conditions is discussed in detail with respect to FIG. 2.

Figure 2:
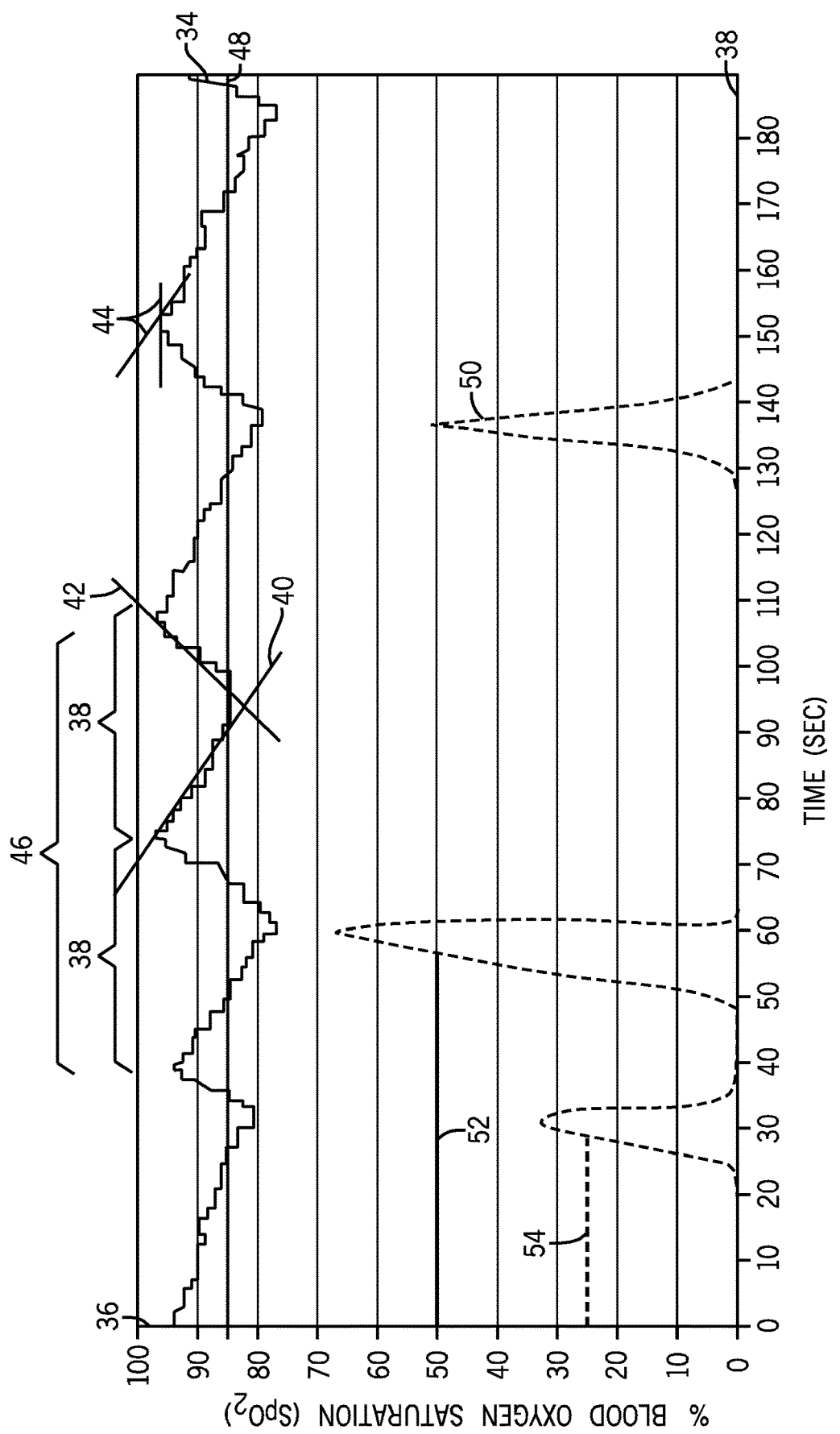
FIG. 2 is a chart of an $SpO_2$ signal over time, illustrating techniques for identifying desaturation patterns, clusters, and low oxygen levels in a patient, in accordance with an embodiment.

FIG. 2 is a chart of a sequence of values representing the blood oxygen saturation ($SpO_2$) of a patient over time, i.e., an $SpO_2$ signal 34. In this chart, a left vertical axis 36 represents the $SpO_2$ level. A horizontal axis 38 represents the time in seconds. In an embodiment, a pattern analysis method may be used to identify obstructive sleep apnea and calculate an airway instability index from the $SpO_2$ signal 34. The method takes advantage of the fact that during each sleep apnea event, e.g., during a single one of the desaturation patterns 38, the blood oxygen level falls slowly, as indicated by reference numeral 40, as oxygen stores in the body are used up and then sharply recovers, as indicated by reference numeral 42, as the patient is aroused and hyperventilates.

The determination of the presence of one or more desaturation patterns 38 may be performed by any number of different techniques. For example, in an embodiment, a single one of the desaturation patterns 38 may be identified by a combination of events, such as when a continuously calculated slope 44 of the $SpO_2$ signal 34 drops to a previously selected value, e.g. −1.5 and the $SpO_2$ signal crosses a predetermined $SpO_2$ level, e.g., 85%. In another embodiment, desaturation patterns 38 may be identified using the methods discussed in U.S. Pat. No. 6,760,608 (hereinafter the '608 patent), incorporated by reference for all purposes as if fully set forth herein. Any number of different numerical values may be used in the determination of the presence of desaturation patterns 38, for example, in embodiments, the value of the slope 44, selected to indicate the start of one of the desaturation patterns 38, may be −0.5, −1.0, −1.5, −2, or any value in between. Further, in embodiments, the predetermined $SpO_2$ level used to indicate the start of one of the desaturation patterns 38 may be 95%, 90%, 85%, 80%, 75%, or any appropriate value in between.

Recurring sleep apnea events may often occur in groups of at least two successive desaturation patterns 38, called a cluster 46. The severity of the apnea may be determined from, for example, the number of desaturation patterns 38 in each cluster 46, the time between each one of the desaturation patterns 38, the slope of the drop 40 in the blood oxygen level during each one of the desaturation patterns 38 or the slope of the recovery 42 of the blood oxygen level as each one of the desaturation patterns 38 ends, among others.

Figure 3:
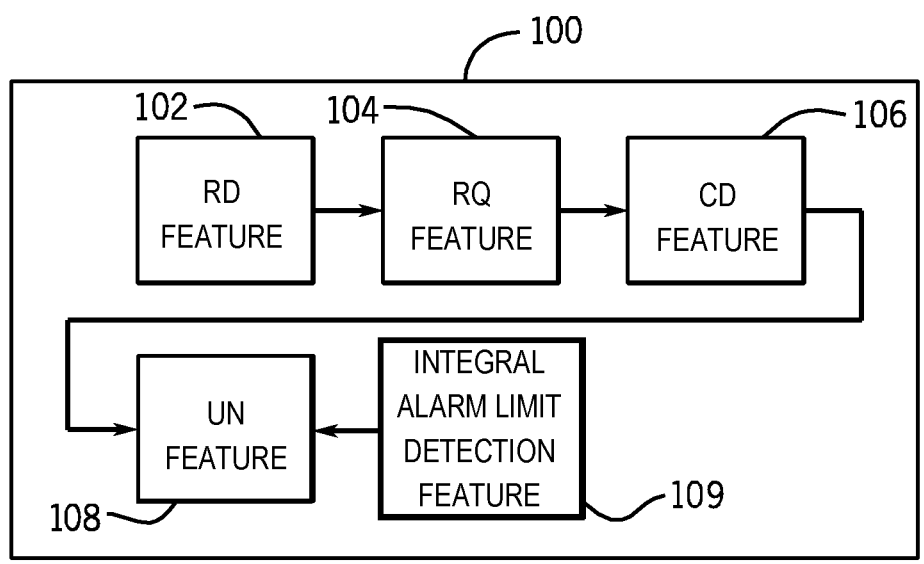
FIG. 3 is a block diagram of an exemplary cluster detection portion of a system.

In an embodiment, a medical monitor or electronic device may include a module or a set of programming instructions for detecting desaturation patterns or clusters or for detecting desturation below certain limits. FIG. 3 is a block diagram of an exemplary cluster detection unit 100 that includes a reciprocation detection (RD) feature 102, a reciprocation qualification (RQ) feature 104, a cluster determination (CD) feature 106, an integral alarm limit detection feature 109, and a user notification (UN) feature 108. Each of these components and the coordination of their functions will be discussed in further detail below.

It should be noted that, in order to detect certain data patterns, embodiments of the present disclosure may utilize systems and methods such as those disclosed in U.S. Pat. No. 6,760,608, U.S. Pat. No. 6,223,064, U.S. Pat. No. 5,398,682, U.S. Pat. No. 5,605,151, U.S. Pat. No. 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006. Accordingly, U.S. Pat. No. 6,760,608, U.S. Pat. No. 6,223,064, U.S. Pat. No. 5,398,682, U.S. Pat. No. 5,605,151, U.S. Pat. No. 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006 are each incorporated herein by reference in their entirety for all purposes.

Figure 4:
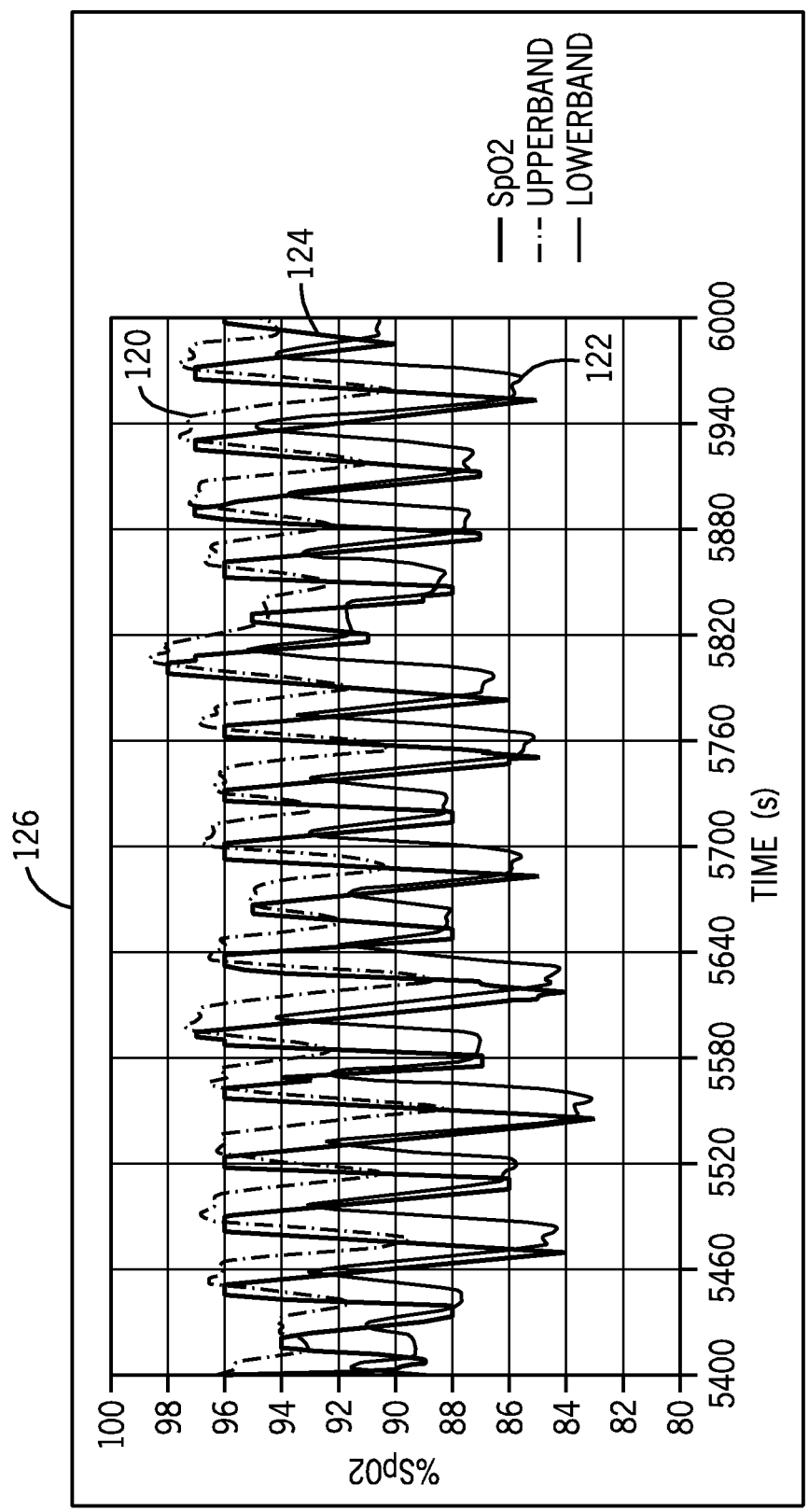
FIG. 4 is an exemplary graph of $SpO_2$ trend data with an upper band and lower band based on mean and standard deviation values.

The RD feature 102 may be capable of performing an algorithm for detecting reciprocations in a data trend. Specifically, the algorithm of the RD feature 102 may perform a statistical method to find potential reciprocation peaks and nadirs in a trend of $SpO_2$ data. A nadir may be defined as a minimum $SpO_2$ value in a reciprocation. The peaks may include a rise peak (e.g., a maximum $SpO_2$ value in a reciprocation that occurs after the nadir) and/or a fall peak (e.g., a maximum $SpO_2$ value in a reciprocation that occurs before the nadir). Once per second, the RD feature 102 may calculate a 12 second rolling mean and standard deviation of the $SpO_2$ trend. Further, based on these mean and standard deviation values, an upper band and lower band 122 with respect to an $SpO_2$ trend 124, as illustrated by the graph 226 in FIG. 4, may be calculated as follows:

Upper Band=mean+standard deviation;

Lower Band=mean−standard deviation.

Once the upper band 120 and lower band 122 have been determined, potential reciprocation peaks and nadirs may be extracted from the $SpO_2$ trend 124 using the upper band 120 and the lower band 124. Indeed, a potential peak may be identified as the highest $SpO_2$ point in a trend segment which is entirely above the upper band 120. Similarly, a potential nadir may be identified as the lowest $SpO_2$ point in a trend segment that is entirely below the lower band 122. In other words, peaks identified by the RD feature 102 may be at least one standard deviation above the rolling mean, and nadirs identified by the RD feature 102 may be at least one standard deviation below the mean. If there is more than one minimum value below the lower band 122, the last (or most recent) trend point may be identified as a nadir. If more than one maximum value is above the upper band 120, the point identified as a peak may depend on where it is in relation to the nadir. For example, regarding potential peaks that occur prior to a nadir (e.g., fall peaks) the most recent maximum trend point may be used. In contrast, for peaks that occur subsequent to a nadir (e.g., rise peaks), the first maximum point may be used. In the example trend data represented in FIG. 4, a peak and nadir is detected approximately every 30-60 seconds.

In one embodiment, a window size for calculating the mean and standard deviation may be set based on historical values (e.g., average duration of a set number of previous reciprocations). For example, in one embodiment, a window size for calculating the mean and standard deviation may be set to the average duration of all qualified reciprocations in the last 6 minutes divided by 2. In another embodiment, an adaptive window method may be utilized wherein the window size may be initially set to 12 seconds and then increased as the length of qualified reciprocations increases. This may be done in anticipation of larger reciprocations because reciprocations that occur next to each other tend to be of similar shape and size. If the window remained at 12 seconds, it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:

Window Size=12(initial value)

else:

RecipDur=½*current qualified recip duration+ ½*previous RecipDur

Window Size=bound(RecipDur,12,36).

With regard to $SpO_2$ signals that are essentially flat, the dynamic window method may fail to find the three points (i.e., a fall peak, a rise peak, and a nadir) utilized to identify a potential reciprocation. Therefore, the RD feature 102 may limit the amount of time that the dynamic window method can search for a potential reciprocation. For example, if no reciprocations are found in 240 seconds plus the current adaptive window size, the algorithm of the RD feature 102 may timeout and begin to look for potential reciprocations at the current $SpO_2$ trend point and later. The net effect of this may be that the RD feature 102 detects potential reciprocations less than 240 seconds long.

Once potential peaks and nadirs are found using the RD feature 102, the RQ feature 104 may pass the potential reciprocations through one or more qualification stages to determine if a related event is caused by ventilatory instability. A first qualification stage may include checking reciprocation metrics against a set of limits (e.g., predetermined hard limits). A second qualification stage may include a linear qualification function. In accordance with present embodiments, a reciprocation may be required to pass through both stages in order to be qualified.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

The metrics referred to above may include fall slope, magnitude, slope ratio, and path length ratio. With regard to fall slope, it may be desirable to limit the maximum fall slope to filter out high frequency artifact in the $SpO_2$ trend, and limit the minimum fall slope to ensure that slow $SpO_2$ changes are not qualified as reciprocations. Regarding magnitude, limits may be placed on the minimum magnitude because of difficulties associated with deciphering the difference between ventilatory instability reciprocations and artifact reciprocations as the reciprocation size decreases, and on the maximum magnitude to avoid false positives associated with sever artifact (e.g., brief changes of more than 35% $SpO_2$ that are unrelated to actual ventilatory instability). The slope ratio may be limited to indirectly limit the rise slope for the same reasons as the fall slope is limited and because ventilatory instability patterns essentially always have a desaturation rate that is slower than the resaturation (or recovery) rate. The path length ratio may be defined as Path Length/((Fall Peak−Nadir)+(Rise Peak−Nadir)), where Path Length=Σ|Current $SpO_2$ Value−Previous $SpO_2$ value| for all $SpO_2$ values in a reciprocation, and the maximum path length ratio may be limited to limit the maximum standard deviation of the reciprocation, which limits high frequency artifact. The following table (Table I) lists the above-identified metrics along with their associated equations and the limits used in accordance with one embodiment:

TABLE I

| Metric | Equation | Minimum | Maximum |
| --- | --- | --- | --- |
| Fall Slope | (Nadir − Fall Peak)/Time between Fall Peak and Nadir | −1.6 (Fast Response Mode) −1 (Normal Response Mode) | −0.08 (Fast Response Mode) −0.05 (Normal Response Mode) |
| Magnitude | Max(Rise Peak, Fall Peak) − Nadir | 3 | 35 |
| Slope Ratio | |Fall Slope/Rise Slope | | 0.05 | 1.75 |
| Path Length Ratio | Path Length = Σ| Current SpO2 Value − Previous SpO2 Value| for all SpO2 values in a Reciprocation. Path Length Ratio = Path Length/((Fall Peak − Nadir) + (Rise Peak − Nadir)) | N/A | 2 |

As indicated in Table I above, an oximetry algorithm in accordance with present embodiments may operate in two response modes: Normal Response Mode or Fast Response Mode. The selected setting may change the $SpO_2$ filtering performed by the oximetry algorithm, which in turn can cause changes in $SpO_2$ patterns. Therefore a saturation pattern detection feature may also accept a response mode so that it can account for the different $SpO_2$ filtering. Table I indicates values associated with both types of response mode with regard to the Fall Slope values.

A second qualification stage of the RQ feature 204 may utilize a object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics described below. The output may be optimized to a maximum value for patterns where ventilatory instability is known to be present. The equation may be optimized to output smaller values (e.g., 0) for other data sets where potential false positive reciprocations are abundant.

To simplify optimization, the equation may be factored into manageable sub-equations. For example, the equation may be factored into sub-equation 1, sub-equation D, and sub-equation 2, as will be discussed below. The output of each sub-equation may then be substituted into the qualification function to generate an output. The outputs from each of the sub-equations may not be utilized to determine whether a reciprocation is qualified in accordance with present embodiments. Rather, an output from a full qualification function may be utilized to qualify a reciprocation. It should be noted that the equations set forth in the following paragraphs describe one set of constants. However, separate sets of constants may be used based on the selected response mode. For example, a first set of constants may be used for the Normal Response Mode and a second set of constants may be used for the Fast Response Mode.

Preprocessing may be utilized in accordance with present embodiments to prevent overflow for each part of the qualification function. The tables (Tables II-VII) discussed below, which relate to specific components of the qualification function may demonstrate this overflow prevention. Each row in a table contains the maximum value of term which is equal to the maximum value of the input variable multiplied by the constant, wherein the term "maximum" may refer to the largest possible absolute value of a given input. Each row in a table contains the maximum intermediate sum of the current term and all previous terms. For example, a second row may contain the maximum output for the second term calculated, as well as the maximum sum of terms 1 and 2. It should be noted that the order of the row may match the order that the terms are calculated by the RQ feature 204. Further, it should be noted that in the tables for each sub-equation below, equations may be calculated using temporary signed 32-bit integers, and, thus, for each row in a table where the current term or intermediate term sum exceeds 2147483647 or is less than −2147483647 then an overflow/underflow condition may occur.

A first sub-equation, sub-equation 1, may use metrics from a single reciprocation. For example, sub-equation 1 may be represented as follows:

Eq1Score=SlopeRatio*SrCf+PeakDiff*PdCf+ FallSlope*FsCf+PathRatio*PrCf+Eq1Offset, where SrCf, PdCf, FsCf, PrCf, and Eq1Offset may be selected using least squares analysis (e.g., using MATLAB®). PeakDiff may be defined as equal to |Recip Fall Peak−Recip Rise Peak|. It should be noted that PeakDiff is typically not considered in isolation but in combination with other metrics to facilitate separation. For example, a true positive reciprocation which meets other criteria but has a high peak difference could be an incomplete recovery. That is, a patient's $SpO_2$ may drop from a baseline to a certain nadir value, but then fail to subsequently recover to the baseline. However, when used in combination with other metrics in the equation, PeakDiff may facilitate separation of two classifications, as large peak differences are more abundant in false positive data sets.

With regard to sub-equation 1, the tables (Tables II and III) set forth below demonstrate that the inputs may be preprocessed to prevent overflow. Further, the tables set forth below include exemplary limits that may be utilized in sub-equation 1 in accordance with present embodiments. It should be noted that Table II includes Fast Response Mode constants and Table III includes Normal Response Mode constants.

change from one reciprocation to the next. Artifact generally has a different signature and tends to be more random with greater variation among reciprocations. For example, the following equation may represent sub-equation D:

EqD=SlopeRatioDiff*SrDCf+DurationDiff*DDCf+
    NadirDiff*NdCf+
    PathLengthRatioDiff*PrDCf_EqDOffset, where, SrDCf, DDCf, NdCf, PrDCf, and EqDOffset may be selected using least squares analysis (e.g., using MAT-LAB®). With regard to other variables in sub-equation D, SlopeRatioDiff may be defined as |Current Recip Slope Ratio−Slope Ratio of last qualified Recip|; DurationDiff may be defined as |Current Recip Duration−Duration of last qualified Recip|; NadirDiff may be defined as |Current Recip Nadir−Nadir value of last qualified Recip|; and PathLengthRatioDiff may be defined as |Current Recip Path Length Ratio−Path Length Ratio of last qualified Recip|.

TABLE II

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| PeakDiff*PdCf | U8 | 100 | None. This value may not exceed 100 since the maximum $SpO_2$ value accepted is 100 | −29282 | −2928200 | −2928200 | NO |
| SlopeRatio*SrCf | U8 | 255 | None | −1534 | −391170 | −3319370 | NO |
| FallSlope*FsCf | S16 | −32768 | None | −19 | 622592 | −2696778 | NO |
| PathRatio*PrCf | U16 | 65535 | None | −7982 | −523100370 | −525797148 | NO |
| Eq1Offset | N/A | N/A | N/A | 809250 | 809250 | −524987898 | NO |

TABLE III

| Term | Variable Type | Maximum Variable Value (a) | Variable Preprocessing | Constant Value (b) (Normal Mode) | Maximum Term Value (a * b) | Maximum Intermediate Sum (Sum of all previous rows) | Overflow |
|---|---|---|---|---|---|---|---|
| PeakDiff*PdCf | U8 | 100 | None. This value may not exceed 100 since the maximum $SpO_2$ value accepted is 100 | −33311 | −3331100 | −3331100 | NO |
| SlopeRatio*SrCf | U8 | 255 | None | −2151 | −548505 | −3879605 | NO |
| FallSlope*FsCf | S16 | −32768 | None | −706 | 23134208 | 19254603 | NO |
| PathRatio*PrCf | U16 | 65535 | None | −6178 | −404875230 | −385620627 | NO |
| Eq1Offset | N/A | N/A | N/A | 576330 | 576330 | −385044297 | NO |

A second sub-equation, sub-equation D, may correspond to a difference between two consecutive reciprocations which have passed the hard limit qualifications checks, wherein consecutive reciprocations include two reciprocations that are separated by less than a defined time span. For example, consecutive reciprocations may be defined as two reciprocations that are less than 120 seconds apart. The concept behind sub-equation D may be that ventilatory instability tends to be a relatively consistent event, with little With regard to sub-equation D, the tables (Tables IV and V) set forth below demonstrate that the inputs may be preprocessed to prevent overflow. Further, the tables set forth below include exemplary limits that may be utilized in sub-equation D in accordance with present embodiments. It should be noted that Table IV includes Fast Response Mode constants and Table V includes Normal Response Mode constants.

TABLE IV

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| EqDOffset | N/A | N/A | N/A | 885030 | 885030 | 885030 | NO |
| SlopeRatioDiff*SrDCf | U8 | 255 | None | −2809 | −716295 | 168735 | NO |
| DurationDiff * DDCf | U16 | 240 | The Recip detection module recips less than or equal to 240 seconds long | −2960 | −710400 | −541665 | NO |
| NadirDiff* NdCf | U8 | 100 | This value may not exceed 100 since the maximum SpO2 value accepted in 100 | −13237 | −1323700 | −1865365 | NO |
| PathLengthRatioDiff *PrDCf | U16 | 65535 | None | 7809 | −511762815 | −513628180 | NO |

TABLE V

| Term | Variable Type | Maximum Variable Value (a) | Variable Preprocessing | Constant Value (b) (Normal Mode) | Maximum Term Value (a * b) | Maximum Intermediate Sum (Sum of all previous rows) | Overflow |
|---|---|---|---|---|---|---|---|
| EqDOffset | N/A | N/A | N/A | 847650 | 847650 | 847650 | NO |
| SlopeRatioDiff *SrDCf | U8 | 255 | None | −2629 | −670395 | 177255 | NO |
| DurationDiff* DDCf | U16 | 240 | The Recip detection module may only detect recips less than or equal to 240 seconds long | −4282 | −1027680 | −850425 | NO |
| NadirDiff* NdCf | U8 | 100 | This value may not exceed 100 since the maximum SpO2 value accepted in 100 | −11705 | −1170500 | −2020925 | NO |
| PathLengthRatioDiff *PrDCf | U16 | 65535 | None | 7844 | −514056540 | −516077465 | NO |

A third sub-equation, sub-equation 2, may combine the output of sub-equation D with the output of sub-equation 1 for a reciprocation (e.g., a current reciprocation) and a previous reciprocation. For example, the following equation may represent sub-equation 2:

Eq2Score=EqDScore*DCf+
Eq1ScoreCurrent*CurrEq1Cf+
Eq1ScorePrev*PrevEq1Cf, where DCf, N1Cf, PrevEq1Cf, and Eq2Offset may be selected using least squares analysis (e.g., using MAT-LAB®). With regard to other variables in sub-equation 2, EqDScore may be described as the output of sub-equation D; Eq1ScoreCurrent may be described as the output of sub-equation 1 for a current reciprocation; and Eq1ScorePrev may be described as the output of sub-equation 1 for the reciprocation previous to the current reciprocation.

With regard to sub-equation 2, the tables (Tables VI and VII) set forth below demonstrate that the inputs may be preprocessed to prevent overflow. Further, the tables set forth below include exemplary limits that may be utilized in sub-equation 2 in accordance with present embodiments. It should be noted that Table VI includes Fast Response Mode constants and Table VII includes Normal Response Mode constants.

TABLE VI

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| Eq2Offset | N/A | N/A | N/A | −2038000 | −203800 | −203800 | NO |
| EqDScore * DCf | S32 | −501590 | The largest output for Sub-equation D may be −513628100 (see Table IV). The input value may be scaled by dividing the value by 1024. Therefore the largest input value may be −501590 | 529 | −265341110 | −265544910 | NO |

TABLE VI-continued

| Term | Variable Type | Maximum Variable Value (a) | Variable Preprocessing | Constant Value (b) (Fast Mode) | Maximum Term Value (a * b) | Maximum Intermediate Sum (Sum of all previous rows) | Overflow |
|---|---|---|---|---|---|---|---|
| Eq1ScorePrev * PrevEq1Cf | S32 | −512683 | The largest output for sub-equation 1 may be −524987898 (see Table II). The input value may be scaled by dividing the value by 1024. Therefore the largest input value may be −512683 | 333 | −170723439 | −436268349 | NO |
| Eq1ScoreCurrent * CurrEq1Cf | S32 | −512683 | Same as previous row | 617 | −316325411 | −752593760 | NO |

TABLE VII

| Term | Variable Type | Maximum Variable Value (a) | Variable Preprocessing | Constant Value (b) (Normal Mode) | Maximum Term Value (a * b) | Maximum Intermediate Sum (Sum of all previous rows) | Overflow |
|---|---|---|---|---|---|---|---|
| Eq2Offset | N/A | N/A | N/A | −194550 | −194550 | −194550 | NO |
| EqDScore * DCf | S32 | −503981 | The largest output for Sub-equation D may be −516077465 (see Table V). The input value may be scaled by dividing the value by 1024. Therefore the largest input value may be −503981 | 532 | −268117892 | −268312442 | NO |
| Eq1ScorePrev * PrevEq1Cf | S32 | −376000 | The largest output for sub-equation 1 may be −385024297 (see Table III). The input value may be scaled by dividing the value by 1024. Therefore the largest input value may be −376000 | 496 | −186496000 | −454808442 | NO |
| Eq1ScoreCurrent * CurrEq1Cf | S32 | −376000 | Same as previous row | 406 | −152656000 | −607464442 | NO |

A qualification function may utilize the output of each of the equations discussed above (i.e., sub-equation 1, sub-equation D, and sub-equation 2) to facilitate qualification and/or rejection of a potential reciprocation. For example, the output of the qualification function may be filtered with an IIR filter, and the filtered output of the qualification function may be used to qualify or reject a reciprocation. An equation for an unfiltered qualification function output in accordance with present embodiments is set forth below:

QFUnfiltered=Eq1Score*SingleRecipWt*Eq2Cf+
N2Score*MultipleRecipWt*Eq2Cf+
NConsecRecip*ConsecCf+RecipMax*MaxCf+
Artifact %*ArtCf+QFOffset, where Eq2Cf, ConsecCf, MaxCf, ArtCf, and QFOffset may be selected using least squares analysis (e.g., using MAT-LAB®), and, as indicated above, Eq1Score may be defined as the output of sub-equation 1.

Other metrics in the unfiltered qualification function include SingleRecipWt, MultipleRecipWt, NConsecRecip, RecipMax, and Artifact %. With regard to SingleRecipWt and MultipleRecipWt, when there are two or more consecutive qualified reciprocations (e.g., qualified reciprocations that are less than 120 seconds apart) present, SingleRecipWt may equal 0 and MultipleRecipWt may equal 1. However, when only a single reciprocation is present, SingleRecipWt may equal 1 and MultipleRecipWt may equal 0.

NConseRecip, which may be defined as equal to max (NConsecRecip',QFConsecMax), may include a count of the number of consecutive reciprocations (e.g., reciprocations that are less than or equal to 120 seconds apart) that have passed the hard limit checks. The value for NConsecRecip may be reset to 0 whenever a gap between any two partially qualified reciprocations exceeds 120 seconds. This may be based on the fact that ventilatory instability is a relatively long lasting event as compared to artifact. Therefore, as more reciprocations pass the hard limit checks, the qualification function may begin qualifying reciprocations that were previously considered marginal. However, to guard against a situation where something is causing a longer term artifact event (e.g., interference from nearby equipment), the value may be clipped to a maximum value to limit the metrics influence on the qualification function output.

RecipMax, which may be defined as equal to max(Fall Peak, Rise Peak), may facilitate making decisions about marginal reciprocations. Indeed, marginal reciprocations with higher maximum SpO$_2$ values may be more likely to get qualified than marginal reciprocations with lower SpO$_2$ values. It should be noted that this metric works in tandem with the NConsecRecip metric, and multiple marginal reciprocations with lower maximum SpO$_2$ values may eventually, over a long period of time, get qualified due to the NConsecRecip metric.

The metric Artifact % may be defined as an artifact percentage that is equal to 100*Total Artifact Count/Recip Duration, where Total Artifact Count is the number of times an artifact flag was set during the reciprocation. Present embodiments may include many metrics and equations that are used to set the artifact flag. Because of this it is a generally reliable indication of the amount of artifact present in the oximetry system as a whole. Marginal reciprocations with a high Artifact % are less likely to be qualified than marginal reciprocations with a low (or 0) artifact percentage.

A last component of the qualification function may include an infinite impulse response (IIR) filter that includes coefficients that may be tuned manually using a tool (e.g., a spreadsheet) that models algorithm performance. The filtered qualification function may be represented by the following equation, which includes different constants for different modes (e.g., Fast Response Mode and Normal Response Mode):

QFFiltered=SingleRecipWt*QFUnfiltered+((1−$a$)
*QFUnfiltered+$a$*PrevQFFiltered)*MultipleRecipWt, where QFUnfiltered may be defined as the current unfiltered qualification function output; PrevQFFiltered may be defined as the previous filtered qualification function output; and where the constat "a" may be set to 0.34 for Fast Response Mode and 0.5 for Normal Response Mode.

The filtered output of the qualification function may be compared to a threshold to determine if the current reciprocation is the result of RAF or artifact. The optimum threshold may theoretically be 0.5. However, an implemented threshold may be set slightly lower to bias the output of the qualification function towards qualifying more reciprocations, which may result in additional qualification of false positives. The threshold may be lowered because, in accordance with present embodiments, a cluster determination portion of the algorithm, such as may be performed by the CD feature 106, may require a certain number (e.g., 5) of fully qualified reciprocations before an index may be calculated, and a certain number (e.g., at least 2) of consecutive qualified reciprocations (with no intervening disqualified reciprocations) within the set of fully qualified reciprocations. Since multiple reciprocations may be required, the clustering detection method may be biased toward filtering out false positives. Accordingly, the reciprocation qualification function threshold may be lowered to balance the two processes.

The CD feature 106 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the detection of clusters. When clustering is not active (e.g., reciprocation count <5) the algorithm may not report the clusters.

The CD feature 106 may utilize various rules to determine the reciprocation count. For example, when the clustering state is inactive, the following rules may be observed:
1.) If the distance between qualified reciprocation exceeds 120 seconds, then the reciprocation count=0;
2.) If the current reciprocation is qualified, and the time from the start of the current reciprocation to the end of the last qualified reciprocation is <=120 seconds, then the reciprocation count=reciprocation count+1;
3.) If the current reciprocation is not qualified, then the reciprocation count=max(reciprocation count−2, 0).

Once clustering is active, it may remain active until the time between two qualified reciprocations exceeds 120 seconds. The following table (Table II) illustrates an example of how the reciprocation count rules may be applied to determine a clustering state.

TABLE VIII

| Current Reciprocation Qualified | Time Since Last Qualified Reciprocation (seconds) | Reciprocation Count | Clustering State |
|---|---|---|---|
| TRUE | N/A | 1 | INACTIVE |
| FALSE | 60 | 0 | INACTIVE |
| TRUE | N/A | 1 | INACTIVE |
| FALSE | 60 | 0 | INACTIVE |
| TRUE | N/A | 1 | INACTIVE |
| TRUE | 30 | 2 | INACTIVE |
| TRUE | 120 | 3 | INACTIVE |
| FALSE | 60 | 1 | INACTIVE |
| TRUE | 10 | 2 | INACTIVE |
| TRUE | 20 | 3 | INACTIVE |
| TRUE | 40 | 4 | INACTIVE |
| FALSE | 30 | 2 | INACTIVE |
| FALSE | 60 | 0 | INACTIVE |
| TRUE | N/A | 1 | INACTIVE |
| TRUE | 20 | 2 | INACTIVE |
| TRUE | 120 | 3 | INACTIVE |
| TRUE | 10 | 4 | INACTIVE |
| FALSE | 90 | 2 | INACTIVE |
| TRUE | 120 | 3 | INACTIVE |
| TRUE | 60 | 4 | INACTIVE |
| TRUE | 20 | 5 | ACTIVE |
| TRUE | 30 | 6 | ACTIVE |
| FALSE | 50 | 6 | ACTIVE |
| FALSE | 100 | 6 | ACTIVE |
| TRUE | 121 | 1 | INACTIVE |
| FALSE | 50 | 0 | INACTIVE |
| TRUE | N/A | 1 | INACTIVE |
| TRUE | 30 | 2 | INACTIVE |
| TRUE | 121 | 1 | INACTIVE |
| TRUE | 10 | 2 | INACTIVE |
| TRUE | 20 | 3 | INACTIVE |
| TRUE | 40 | 4 | INACTIVE |
| TRUE | 40 | 5 | ACTIVE |

In addition to cluster detection, embodiments may also include an integral alarm limit detection feature 109 that is configured to detect if the SpO$_2$ signal 34 drops below a lower limit 48. In the embodiment shown in FIG. 4, this limit 48 may be set at an SpO$_2$ level of 85%. In other embodiments, the level may be 95%, 90%, 80%, 75%, or any other appropriate value selected by the practitioner based on the patient's condition.

The use of an absolute limit, however, may result in numerous alarms that are not necessarily informative. Accordingly, methods may be used to determine the severity of the condition and only alert the practitioner if the condition persists. For example, in an embodiment, the integral alarm limit detection feature 109 may calculate an integral 50 from the SpO$_2$ signal 34 by using a summation of the time the signal 34 may be below the lower limit 48 multiplied by the amount the signal 34 may be below the lower limit 48. Similarly, an upper limit (not shown) may also be used for calculating the integral 50. An integral alarm limit 52 may be selected for alerting a practitioner based on the value of the integral 50. In embodiments, calculation of the integral 50 may be performed by the methods detailed in U.S. Pat. No. 5,865,736 (hereinafter the '736 patent), which is hereby incorporated by reference as if fully set forth herein.

The integral alarm limit detection feature 109 and the CD feature 106 may provide reports or other indications to a user notification feature 108 that may be configured to alert a user if there is one or more of a cluster detection or integral alarm limit violation. Referring back to FIG. 2, a combined alarm limit 54 may be based on both the presence of desaturation patterns 38, or clusters 46 (e.g., clusters determined by any suitable method), and the value of the integral 50. In this embodiment, if desaturation patterns 38, or clusters 46, are present and the integral 50 reaches the value of the combined alarm limit 54 an alert may be activated. In an embodiment, the limit for the combined alarm 54 may not be directly set by a practitioner, but may instead by calculated from the value of other parameters set by the practitioner. For example, the value of the combined alarm limit 54 may be calculated using the formula given in equation 1:

$$CAL = CAS*IAL/100 \qquad \text{equation 1.}$$

In this equation, CAL may be the combined alarm limit 54, CAS may be a combined alarm sensitivity set by the user, and IAL may be the integral alarm limit 52 discussed above.

Figure 5:
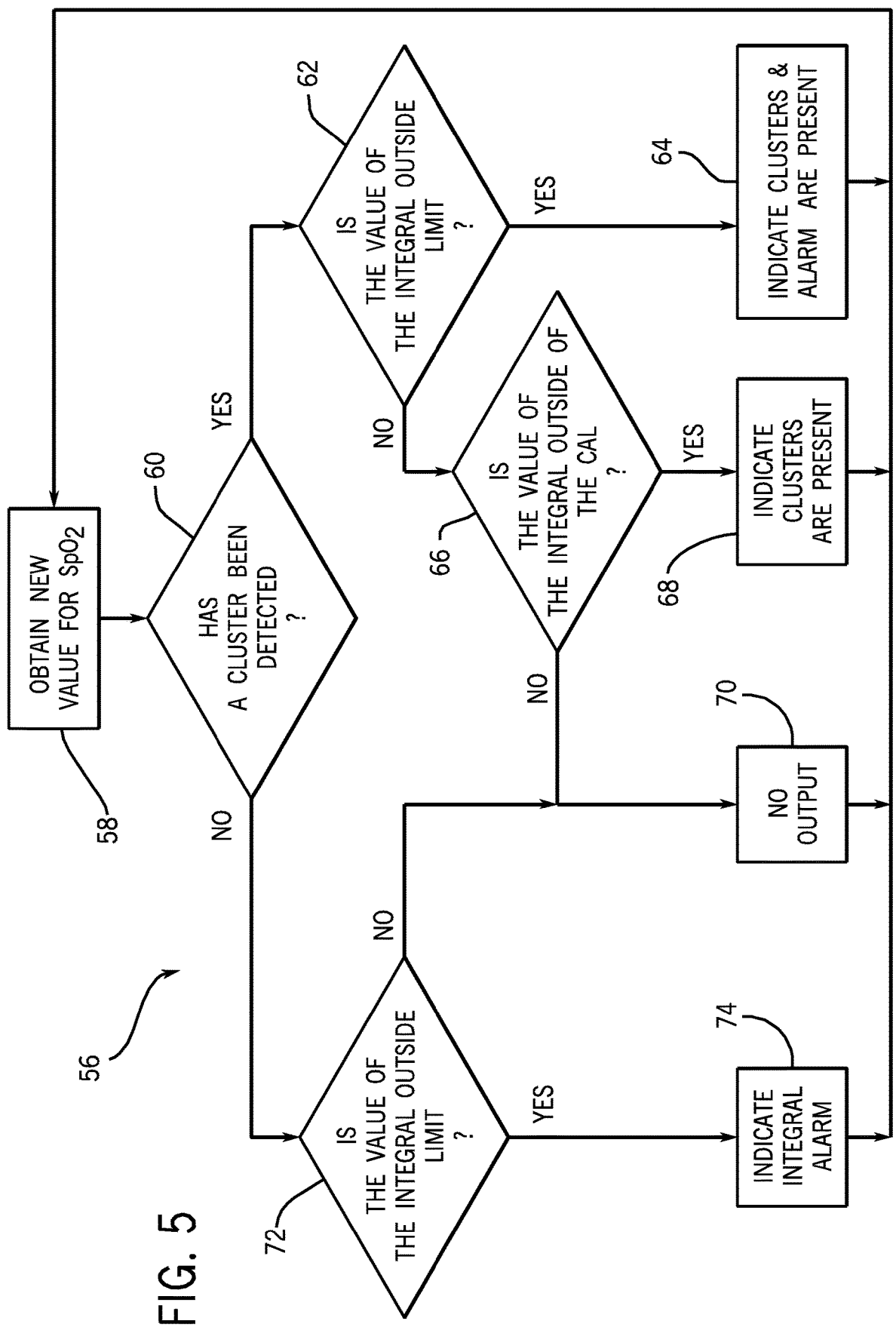
FIG. 5 is a process flow chart showing a method for alerting practitioners to the presence of certain physiological conditions, in accordance with an embodiment.

FIG. 5 is a process flow chart showing a method 56 for alerting practitioners to the presence of certain physiological conditions, in accordance with an embodiment. Referring also to FIG. 2, the method 56 of FIG. 5 starts with the collection of a new sample for the $SpO_2$ signal 34, as shown in block 58. As shown in block 60, the $SpO_2$ signal 34 may be analyzed to determine if a new cluster 46, e.g., two or more of the desaturation patterns 38 in sequence or a cluster as detected by a programmed functional unit 100, has been detected. In other embodiments, the method 56 may be configured to determine if only one of the desaturation patterns 38 may be detected. If a cluster 46 has been detected, the method 56 proceeds to block 62, to determine if the integral 50 has reached the integral alarm limit 52. If so, as shown in block 64, the method 56 may inform a practitioner that the integral alarm limit 52 has been reached and clusters 46 are present in the $SpO_2$ signal 34. The method 56 may then return to block 58 to collect the next $SpO_2$ sample in the $SpO_2$ signal 34.

If no integral alarm condition has been detected in block 62, the method may determine if the combined alarm limit 54 has been reached by the integral 50, as shown in block 66. The combined alarm limit 54 may be calculated using the method discussed with respect to equation 1. Further, the combined alarm limit 54 may be set to zero, which would inform the user of the presence of clusters 46, even if the value for the integral 50 was zero. If the combined alarm limit 54 has been reached, the method 56 may inform a practitioner that clusters 46 are present, as shown in block 68. If the combined alarm limit 54 has not been reached, the method 56 may activate no alerts, as shown in block 70. After either blocks 68 or 70, the method 56 may return to block 58 to collect the next $SpO_2$ sample in the $SpO_2$ signal 34.

If a cluster 46 may be not detected in block 60, the method 56 may still determine if the integral 50 has reached the integral alarm limit 52, as shown in block 72. If the integral 50 has not reached the integral alarm limit 52, no alarm may be activated, as shown in block 70. However, if the integral 50 has reached the integral alarm limit 52, the method 56 may inform a practitioner that the integral alarm limit 52 has been reached, as shown in block 74. After activating the alert, the method 56 may return to block 58 to collect the next $SpO_2$ sample in the $SpO_2$ signal 34.

The operation of an embodiment of the method 56 discussed with respect to FIG. 5 may be illustrated by the charts shown in FIGS. 6-9. In each of these charts, as in FIG. 2, the $SpO_2$ signal 34 may be plotted against the percent blood oxygen saturation level ($SpO_2$) on the left vertical axis 36 and the time, in seconds, on the horizontal axis 38. The horizontal line at a value of 85% on the $SpO_2$ axis 36 represents the lower limit 48 that may be used for controlling alarms or in the calculation of the integral 50. The value for the integral 50 may be plotted on each chart, showing the response of the method under the conditions described. An alarm condition indicator line 76 may be used to visually indicate the presence of an alarm condition, for example, when the value of the integral 50 exceeds the combined alarm limit 54 or the integral alarm limit 52. In embodiments, other indicators of the alarm status may be used in addition to, or in place of, the alarm condition indicator line 76. For example, audible alerts on the local unit 10 or on devices attached to a local area network 28, as discussed with respect to FIG. 1, may be activated.

Figure 6:
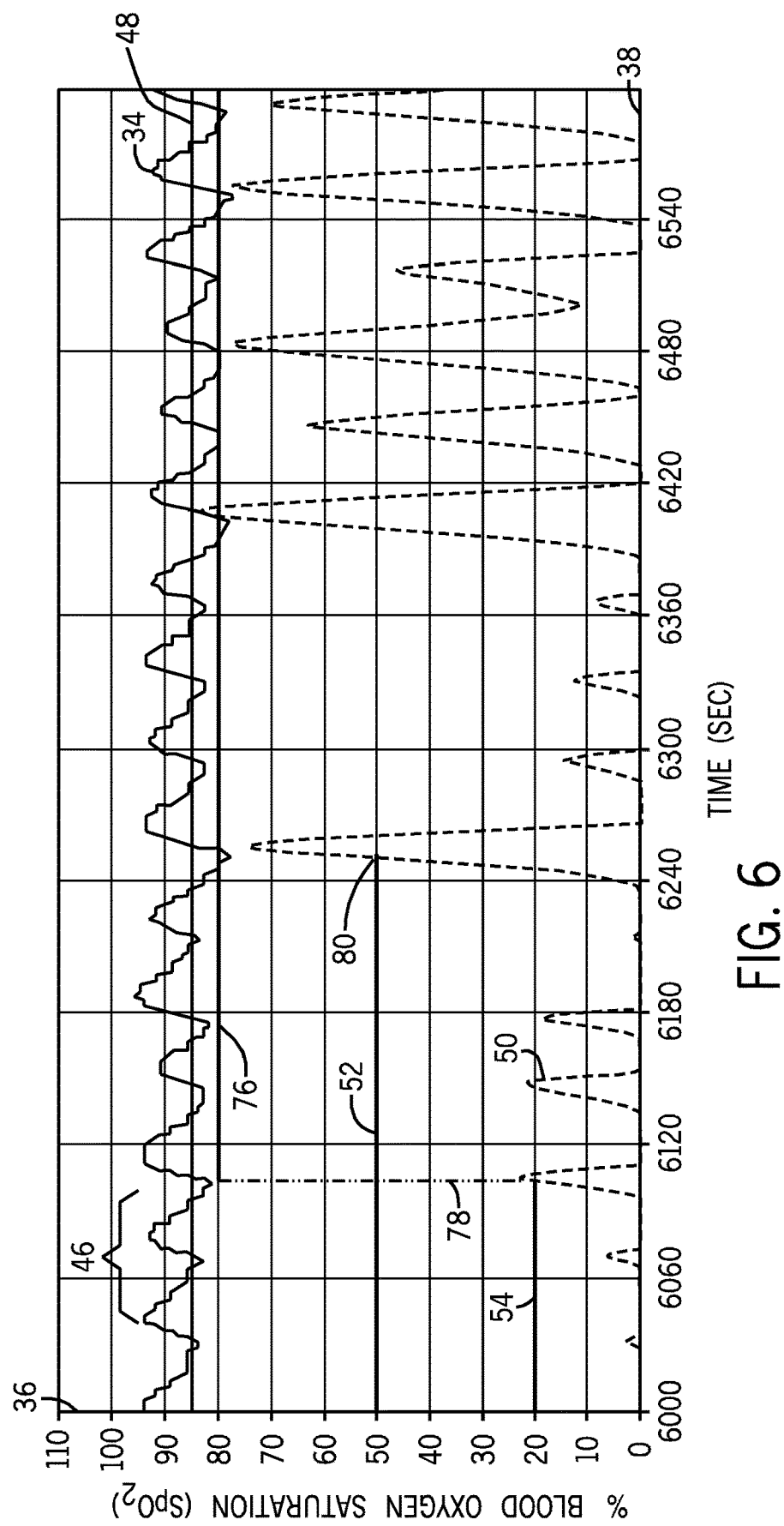
FIG. 6 is a chart useful in explaining the operation of the method of FIG. 5 to alert a practitioner to the presence of desaturation patterns when an integral representing blood oxygen saturation crosses a combined alarm limit, in accordance with an embodiment.

FIG. 6 is a chart of an $SpO_2$ signal 34 that may illustrate the operation of an embodiment. In this example, a practitioner may wish to be informed of the presence of clusters before the value of the integral 50 has reached the integral alarm limit 52, but does not want to be informed of short duration desaturation events. To achieve this, the practitioner may set the integral alarm limit 52 to 50 and the combined alarm sensitivity to 40%. Using equation 1, this provides a value of 20% for the combined alarm limit 54. The value for the integral 50 reaches the combined alarm limit 54 at about 6105 seconds, as indicated by reference numeral 78, which may result in the presence of the alarm condition indicator line 76. Although the value of the integral 50 later reaches the integral alarm limit 52, as indicated by reference numeral 80, the method 56 has already activated an alarm condition and no further alarm may be activated. However, in other embodiments, a further alarm condition may be activated to indicate the possible presence of a more severe condition. This could be performed, for example, by changing the color of the alarm condition indicator line 78 from yellow to red, by pulsing an audible alarm, or any combination thereof.

Figure 7:
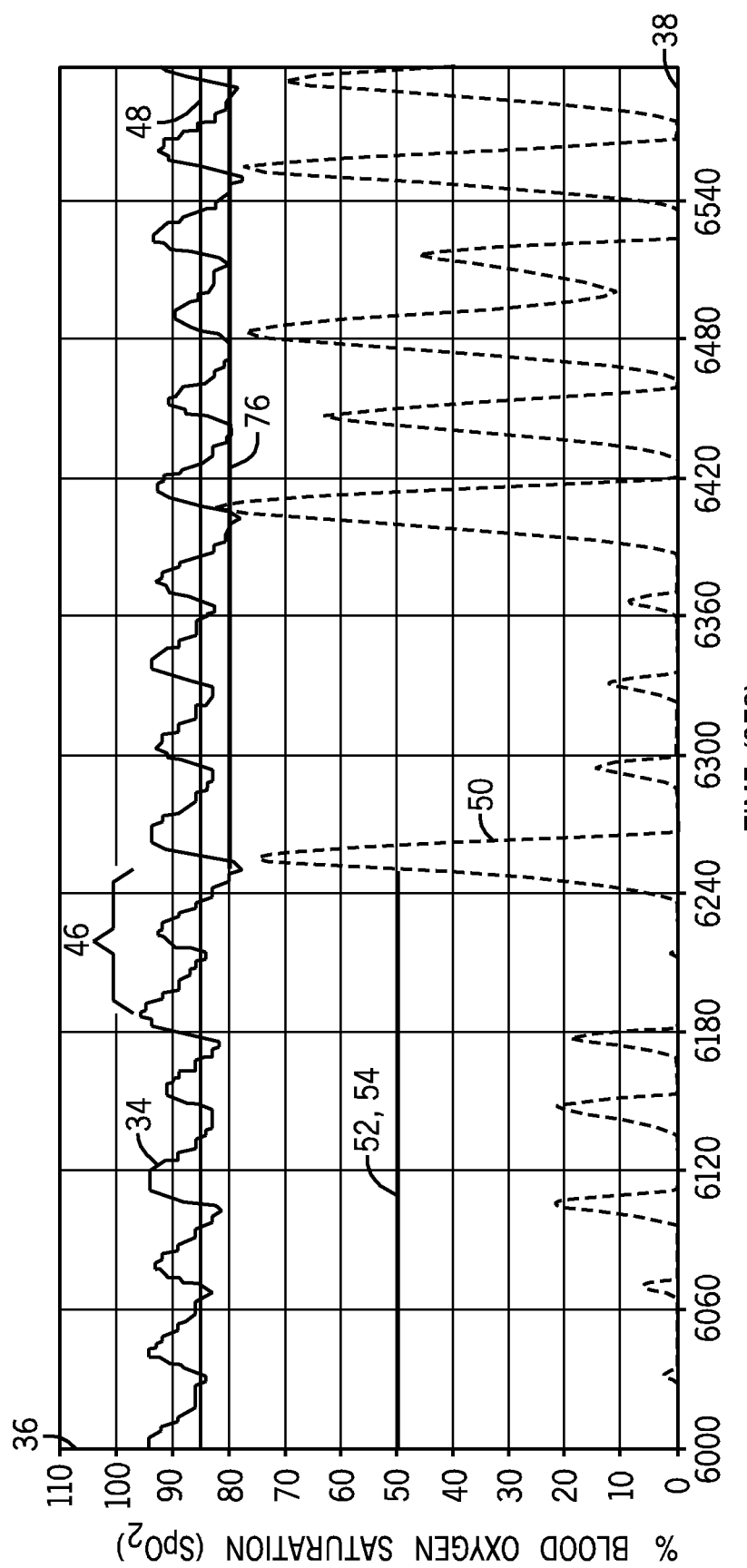
FIG. 7 is a chart useful in explaining the performance of the method of FIG. 5 when a user has chosen to ignore desaturation patterns unless an integral representing blood oxygen saturation crosses an integral alarm limit, in accordance with an embodiment.

FIG. 7 is another chart of the $SpO_2$ signal 34 that may illustrate the operation of an embodiment. A practitioner may not wish to be informed of the presence of clusters 46 unless the integral 50 has reached the integral alarm limit 52. To achieve this, the practitioner may set the combined alarm sensitivity to 100%. If the integral alarm limit 52 is set to 50, equation 1 would provide a combined alarm limit 54 that is at 50%. As shown in FIG. 7, when the value for the integral 50 reaches 50%, both the integral alarm limit 52 and the combined alarm limit 54 are simultaneously activated, resulting in the presence of the alarm condition indicator line 76.

Figure 8:
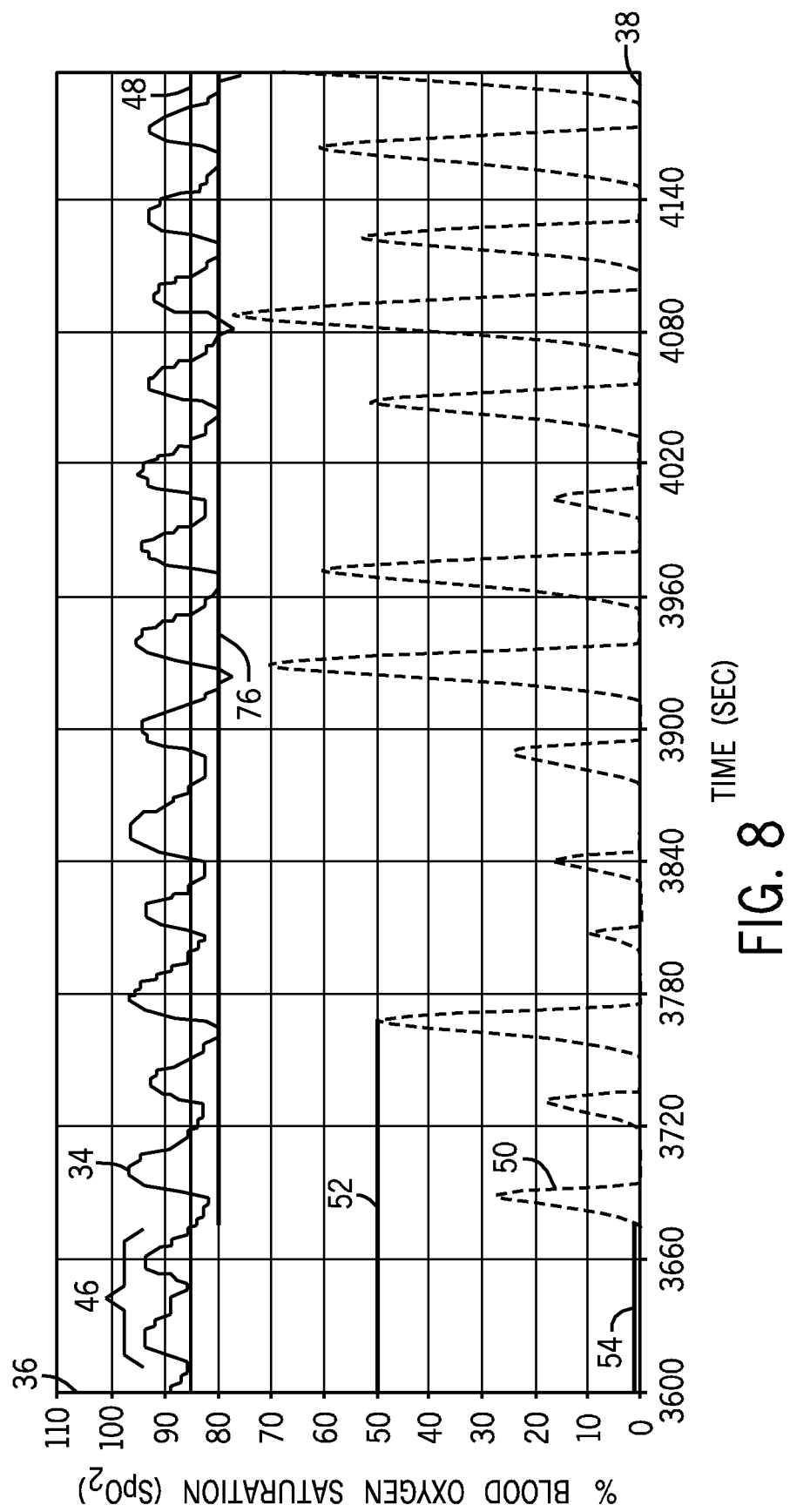
FIG. 8 is a chart useful in explaining the performance of the method of FIG. 5 when a user has chosen to be alerted to the presence of desaturation patterns whenever the $SpO_2$ signal is below a lower limit, in accordance with an embodiment.

FIG. 8 is another chart of the $SpO_2$ signal 34 that may illustrate the operation of an embodiment. A practitioner may wish to be informed anytime there are clusters 46 present in the $SpO_2$ signal 34 and the $SpO_2$ value drops below the lower limit 48. To achieve this, the practitioner may set the combined alarm sensitivity to 1%. If the value for the integral alarm limit 52 is set to 50, equation 1 would provide a value of 0.5% for the combined alarm limit 54. Accordingly, the method 56 would display the alarm condition indicator line 76 if clusters 46 are present and the value of the integral 50 is greater than 0.5%. Thus, the alarm condition would be indicated well before the value of the integral 50 reached the integral alarm limit 52.

Figure 9:
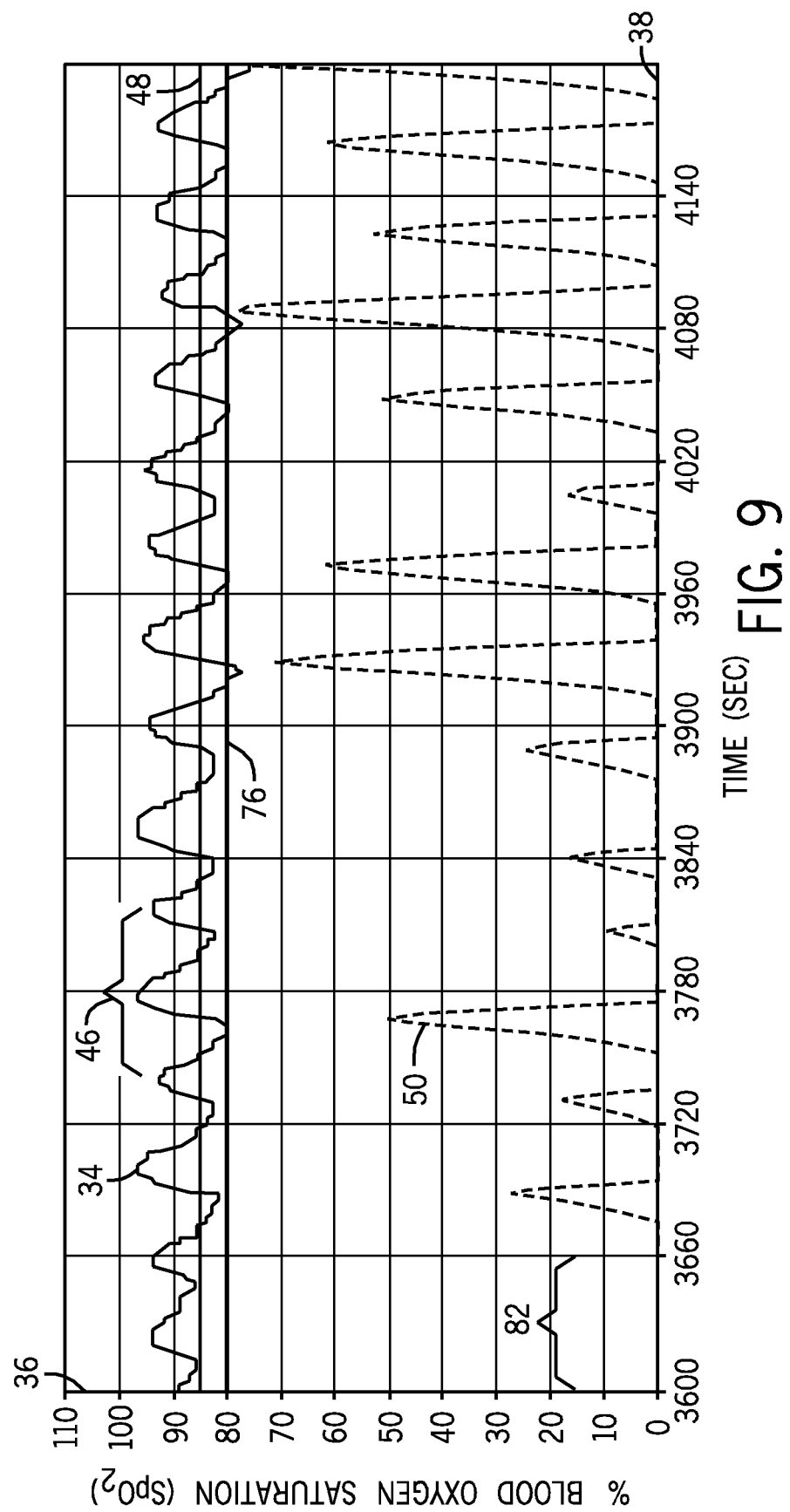
FIG. 9 is a chart useful in explaining the performance of the method of FIG. 5 when a user has chosen to be alerted to the presence of desaturation patterns under any blood oxygen condition, in accordance with an embodiment.

FIG. 9 is another chart of the $SpO_2$ signal 34 that may illustrate the operation of an embodiment. In this example, a practitioner may wish to be informed of the presence of clusters 46 anytime they are present, regardless of the value of the integral 50. Accordingly, the practitioner may set the value for the combined alarm sensitivity to 0%. Thus, the alarm conditioner indicator line 76 is present anytime clusters 46 are present, including during periods in which the value of the integral 50 may be zero, as indicated by reference numeral 82.

While the disclosure is suitable to various modifications and alternative forms, embodiments have been shown by way of example in the drawings and have been described in detail herein. However, it should be understood that the disclosure is not intended to be limited to the particular forms disclosed. Rather, the disclosure is intended to encompass all modifications, equivalents, and alternatives falling within the spirit and scope of this disclosure as defined by the following appended claims.

What is claimed is:

1. A system, comprising: a processor configured to:
determine a presence of a plurality of oxygen desaturation patterns in a photoplethsymograph (PPG) signal;
determine that a first oxygen desaturation pattern of the plurality of oxygen desaturation patterns is qualified based on a qualification function;
adjust the qualification function in response to determining that the first oxygen desaturation pattern is qualified;
determine that a second oxygen desaturation pattern of the plurality of oxygen desaturation patterns is qualified based on the adjusted qualification function, wherein the adjusted qualification function is less stringent than the qualification function, and wherein the second oxygen desaturation pattern is not qualified based on the qualification function but is qualified based on the adjusted qualification function; and
trigger a sleep apnea alarm in response to the determination that the first oxygen desaturation pattern and the second oxygen desaturation pattern are qualified.

2. The system of claim 1, wherein the processor is configured to count consecutive qualified desaturation patterns and to trigger the sleep apnea alarm in response to a count above a predetermined alarm count threshold.

3. The system of claim 2, wherein the processor is configured to adjust the qualification function in response to the count of the consecutive desaturation patterns being above a predetermined qualification count.

4. The system of claim 1, wherein the qualification function is based on: a slope ratio between the fall slope and the rise slope of a desaturation pattern;
a magnitude of the desaturation pattern between a rise peak and a fall peak; a fall slope of the desaturation pattern between a fall peak and a nadir;
a path length ratio of the desaturation pattern;
a difference between consecutive desaturation patterns; or a combination thereof.

5. The system of claim 1, comprising a PPG sensor configured to generate the PPG signal.

6. The system of claim 1, wherein the processor is configured to increase an air pressure supplied by the system in response to triggering the sleep apnea alarm.

7. The system of claim 1, wherein the processor is configured to adjust the qualification function to qualify desaturation patterns having maximum oxygen saturations above a threshold.

8. A system, comprising:
a photoplethsymograph (PPG) sensor configured to generate a PPG signal; and a patient monitor comprising:
a processor configured to:
receive the PPG signal from the PPG sensor;
determine a presence of one or more oxygen desaturation patterns in a photoplethsymograph (PPG) signal;
determine that a first oxygen desaturation pattern of the one or more oxygen desaturation patterns is indicative of sleep apnea based on at least a predetermined range or a predetermined threshold;
increase a count of consecutive desaturation patterns in response to determining that the first oxygen desaturation pattern is indicative of sleep apnea based on the predetermined range or the predetermined threshold, wherein the first oxygen desaturation pattern is within a predetermined time period;
adjust a qualification function based on the count of consecutive desaturation patterns;
determine that a second oxygen desaturation pattern is indicative of sleep apnea, and wherein the second oxygen desaturation pattern is not qualified based on the qualification function but is qualified based on the adjusted qualification function; and
provide an indication of sleep apnea in response to determining that both the first oxygen desaturation pattern and the second oxygen desaturation pattern are indicative of sleep apnea.

9. The system of claim 8, comprising a display coupled to the processor, wherein the processor is configured to provide the indication of sleep apnea as a visual indicator on the display.

10. The system of claim 8, comprising a mask operatively coupled to the processor, wherein the processor is configured to increase an air pressure supplied by the system via the mask in response to providing the indication of sleep apnea.

11. The system of claim 8, comprising a network interface operatively coupled to the processor and configured to send the indication of sleep apnea to a device located on a local area network.

12. The system of claim 8, wherein the first oxygen desaturation pattern and the second oxygen desaturation pattern are part of a cluster of the one or more oxygen desaturation patterns in the PPG signal.

13. The system of claim 8, wherein the processor is configured to:
determine a value for an integral in response to a determination that the PPG signal is outside of a PPG range or a PPG threshold;
compare the value of the integral to an integral threshold; and
provide the indication of sleep apnea based on a result of the comparing and the determination that first oxygen desaturation pattern and the second oxygen desaturation pattern are indicative of sleep apnea.

14. A method, comprising:
determining, via the processor, a presence of one or more oxygen desaturation patterns in a photoplethsymograph (PPG) signal;
adjusting, via the processor, a qualification function in response to a determination that a first oxygen desaturation pattern of the one or more oxygen desaturation patterns is indicative of sleep apnea;
determining, via the processor, that a second oxygen desaturation pattern of the plurality of oxygen desaturation patterns is indicative of sleep apnea, and wherein the second oxygen desaturation pattern is not qualified based on the qualification function but is qualified based on the adjusted qualification function;
determining, via the processor, a presence of a cluster based on determining that both the first oxygen desaturation pattern and the second oxygen desaturation pattern are indicative of sleep apnea;

determining, via the processor, a value for an integral in response to a determination that the PPG signal is outside of a PPG range or a PPG threshold; and providing, via the processor, an indication of sleep apnea in response to the cluster detection and the value being above a combined alarm limit associated with cluster detection.

15. The method of claim 14, wherein the combined alarm limit is lower than an integral alarm threshold associated with no cluster detection.

16. The method of claim 14, wherein the indication of sleep apnea is an alarm.

17. The method of claim 14, wherein the indication of sleep apnea is displayed on a display.

18. The method of claim 14, comprising increasing, via the processor, an air pressure supplied by a system in response to the indication of sleep apnea.

19. The method of claim 14, comprising: generating, via a PPG sensor, the PPG signal; and receiving, via the processor, the PPG signal from the PPG sensor.

* * * * *